United States Patent
Bor et al.

(10) Patent No.: US 10,945,834 B2
(45) Date of Patent: Mar. 16, 2021

(54) HYPERCHROMATIC PRESYBYOPIA-CORRECTING INTRAOCULAR LENSES

(71) Applicant: Alcon Inc., Fribourg (CH)

(72) Inventors: Zsolt Bor, San Clemente, CA (US); Mikhail Ovchinnikov, Dana Point, CA (US)

(73) Assignee: Alcon Inc., Fribourg (CH)

( * ) Notice: Subject to any disclaimer, the term of this patent is extended or adjusted under 35 U.S.C. 154(b) by 39 days.

(21) Appl. No.: 16/158,732

(22) Filed: Oct. 12, 2018

(65) Prior Publication Data

US 2019/0110889 A1    Apr. 18, 2019

Related U.S. Application Data

(60) Provisional application No. 62/571,821, filed on Oct. 13, 2017.

(51) Int. Cl.
*A61F 2/16* (2006.01)
*G02C 7/04* (2006.01)
*G02B 5/18* (2006.01)

(52) U.S. Cl.
CPC .......... *A61F 2/1654* (2013.01); *A61F 2/1618* (2013.01); *G02C 7/044* (2013.01); *A61F 2/1635* (2013.01); *A61F 2/1637* (2013.01); *G02B 5/1895* (2013.01); *G02C 2202/20* (2013.01); *G02C 2202/22* (2013.01)

(58) Field of Classification Search
CPC .... A61F 2/1654; A61F 2/1618; A61F 2/1635; A61F 2/1637; G02C 7/044; G02C 2202/20; G02C 2202/22; G02B 5/1895
See application file for complete search history.

(56) References Cited

U.S. PATENT DOCUMENTS

| 5,054,905 A | 10/1991 | Cohen |
| 5,129,718 A | 7/1992 | Futhey |
| 2010/0097569 A1* | 4/2010 | Weeber ................. A61F 2/1618 351/159.44 |
| 2010/0312337 A1* | 12/2010 | Zhang .................. A61F 2/1613 623/6.31 |

OTHER PUBLICATIONS

Franchini, "Compromise between spherical and chromatic aberration and depth of focus in aspheric intraocular lenses", J Cataract Refract Surg, 2007, 33:497-509.
(Continued)

*Primary Examiner* — David H Willse
*Assistant Examiner* — Tiffany P Shipmon

(57) ABSTRACT

An ophthalmic device includes at least one ophthalmic lens and at least one diffractive structure for the at least one ophthalmic lens. The ophthalmic lens(es) have at least one base focal length and a base power for a first wavelength of visible light. The diffractive structure(s) have a chromatic aberration such that the diffractive structure(s) have a first power for the first wavelength of visible light and a second power for a second wavelength of visible light. A difference between the first power and the second power is at least two diopters.

13 Claims, 4 Drawing Sheets

(56) References Cited

OTHER PUBLICATIONS

Negishi et al., "Effect of Chromatic Aberration on Contrast Sensitivity in Pseudophakic Eyes", (Reprinted) Arch Ophthalmol, 2001, 119:1154-1158.
Nio et al., "Effect of intraocular lens implantation on visual acuity, contrast sensitivity, and depth of focus", J Cataract Refract Surg, 2003, 29:2073-2081.
Ravikumar et al., "Calculation of retinal image quality for polychromatic light", J. Opt. Soc. Am. A, 2008, 25 (10)2395-2407.
Ravikumar et al., "Chromatic aberration and polychromatic image quality with diffrative multifocal intraocular lenses", J Cataract Refract Surg, 2014, 40:1192-1204.
Thibos et al., "Theory and Measurement of Ocular Chromatic Aberration", Vision Res., 1990, 30 (1):33-49.
Weeber et al., "Extending the range of vision using diffractive intraocular lens technology", J Cataract Refract Surg, 2015, 41:2746-2754.
Whitefoot and Charman, "Hyperchromatic lenses as potential aids for the presbyope", Ophthal. Physiol. Opt., 1995, 15(1):13-22.
Zhao and Mainster, "The effect of chromatic dispersion on pseudophakic optical performance", Br J Ophthalmol, 2007, 91:1225-1229.

\* cited by examiner

HYPERCHROMATIC PRESYBYOPIA-CORRECTING INTRAOCULAR LENSES

FIELD

The present disclosure relates generally ophthalmic lenses and, more particularly, to hyperchromatic presbyopia-correcting intraocular lenses.

BACKGROUND

Intraocular lenses (IOLs) are implanted in patients' eyes either to replace a patient's lens or to complement the patient's lens. The IOL may be implanted in place of the patient's lens during cataract surgery. Alternatively, an IOL may be implanted in a patient's eye to augment the optical power of the patient's own lens.

Some conventional IOLs are monofocal, while others are multifocal. Monofocal IOLs have single power, which generally provides a patient with good distance vision. Although monofocal IOLs provide a singe focus (e.g., distance vision), a depth of focus of the IOL may still provide the patient with acceptable vision for a range of distances around the single focus. Multifocal IOLs have multiple powers. For example, a bifocal IOL has two powers (e.g., a base power and an add power) for improving vision in two ranges (e.g., distance vision may be provided by the base power while near vision is provided by the add power). Thus, a bifocal IOL may improve both a patient's distance vision and near vision. Because multifocal IOLs may provide a near focus, they may reduce the patient's need for glasses after surgery and thus may be considered "presbyopia-correcting."

In addition to benefits noted above, IOLs may also be designed to reduce chromatic aberration, a phenomenon resulting from the fact that different wavelengths of light refract at slightly different angles and thus focus at different points. To reduce the blur resulting from chromatic aberration, IOLs may have optical designs aimed at reducing chromatic aberration (i.e., reducing the distance between the focal points of various wavelengths of light). For example, IOLs may be designed such that the total chromatic aberration is less than 1.5 diopters.

Although multifocal IOLs may beneficially provide presbyopia correction as noted above, they may also suffer from various drawbacks. For example, for most multifocal IOLs, the light entering the eye is split for vision at different distances. For example, light near the center of the eye may be used for near vision (as the pupil tends to constrict for near vision) while light near the periphery of the lens of the IOL may be used for far vision. As a result, less light is available for any particular type of vision (as compared to a monofocal IOL where all light is directed to a single focal point), which may adversely impact visual acuity. As another example, multifocal IOLs may require high centration accuracy. For an additional 3 diopters in near power, the x-y centration of the IOL may be less than one minute of angle, a level of accuracy that may be technically challenging. Visual acuity may be again sacrificed. Moreover, the distribution of energy between the near and far vision for a multifocal IOL depends upon the pupil size. This variation may be undesirable.

Accordingly, what is needed is an IOL having an improved depth of field have the visual acuity drawbacks associated with conventional multifocal IOLs.

SUMMARY

An ophthalmic device includes at least one ophthalmic lens and at least one diffractive structure for the at least one ophthalmic lens. The ophthalmic lens(es) have at least one base focal length and a base power for a first wavelength of visible light. The diffractive structure(s) have a chromatic aberration such that the diffractive structure(s) have a first power for the first wavelength of visible light and a second power for a second wavelength of visible light. A difference between the first power and the second power is at least two diopters.

The lens may have the diffractive structure(s) described above may have sufficiently high chromatic aberration such that the ophthalmic device may be used to correct near vision. As a result, performance may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular devices provided in particular implementations. However, devices will operate effectively in other implementations. For example, the devices are described primarily in terms of IOLs. However, the devices may be used with contact lenses. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or fewer components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device that includes at least one ophthalmic lens and at least one diffractive structure for the at least one ophthalmic lens. The ophthalmic lens(es) have at least one base focal length and a base power for a first wavelength of visible light. The diffractive structure(s) have a chromatic aberration such that the diffractive structure(s) have a first power for the first wavelength of visible light and a second power for a second wavelength of visible light. A difference between the first power and the second power is at least two diopters.

Figure 1A:
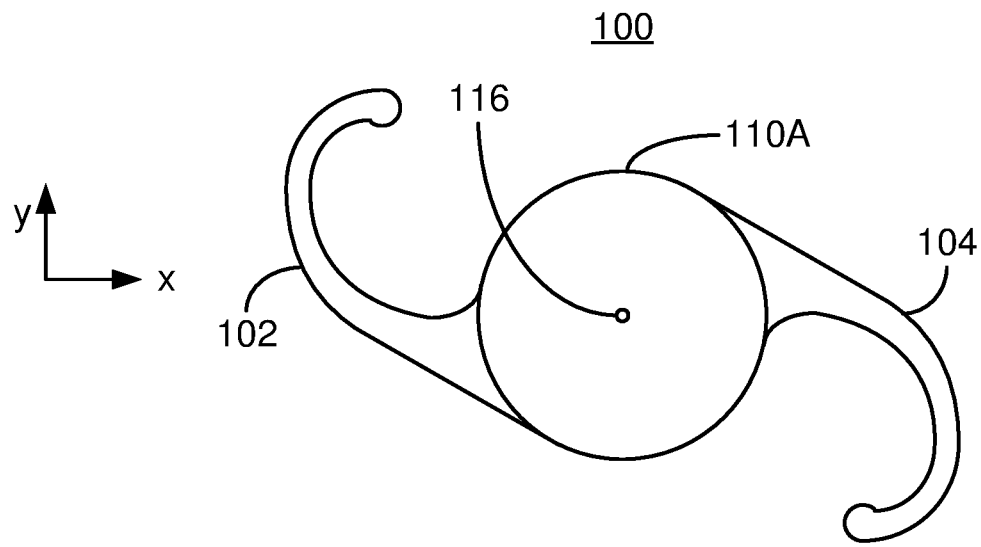
FIGS. 1A-1D depict plan and side views of and ray diagrams for an exemplary embodiment of an ophthalmic device that includes a hyperchromatic lens.
Figure 1B:
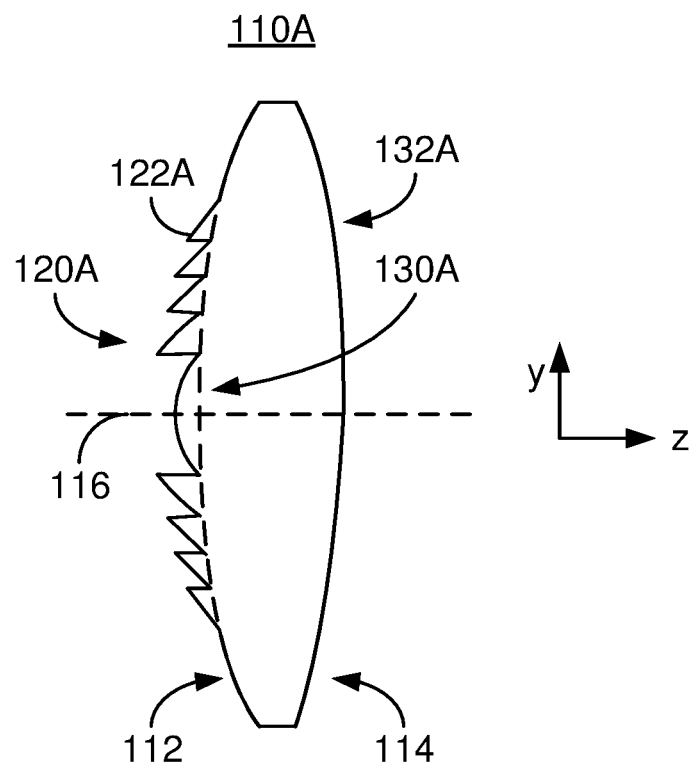
Figure 1C:
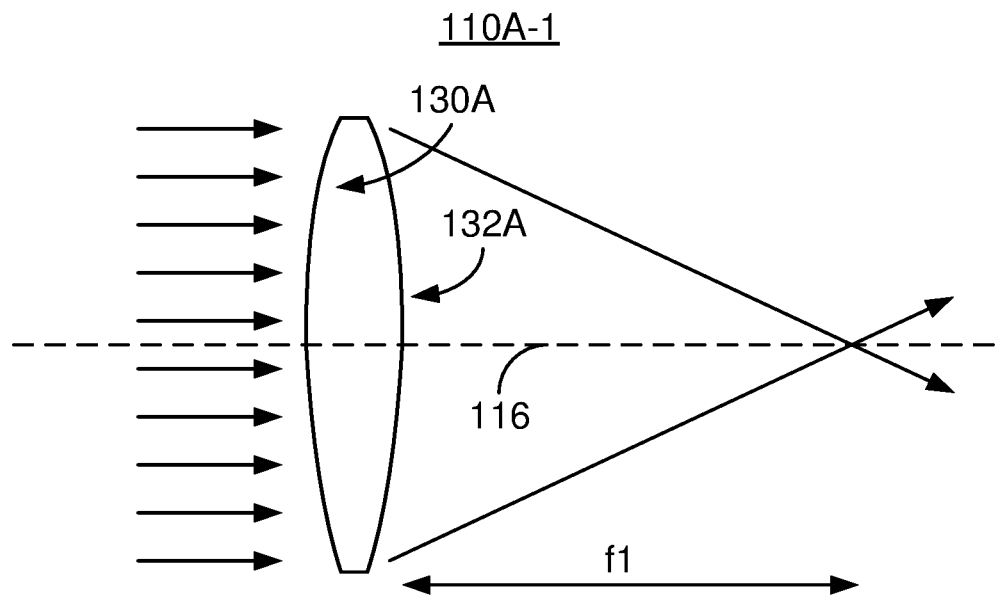
Figure 1D:
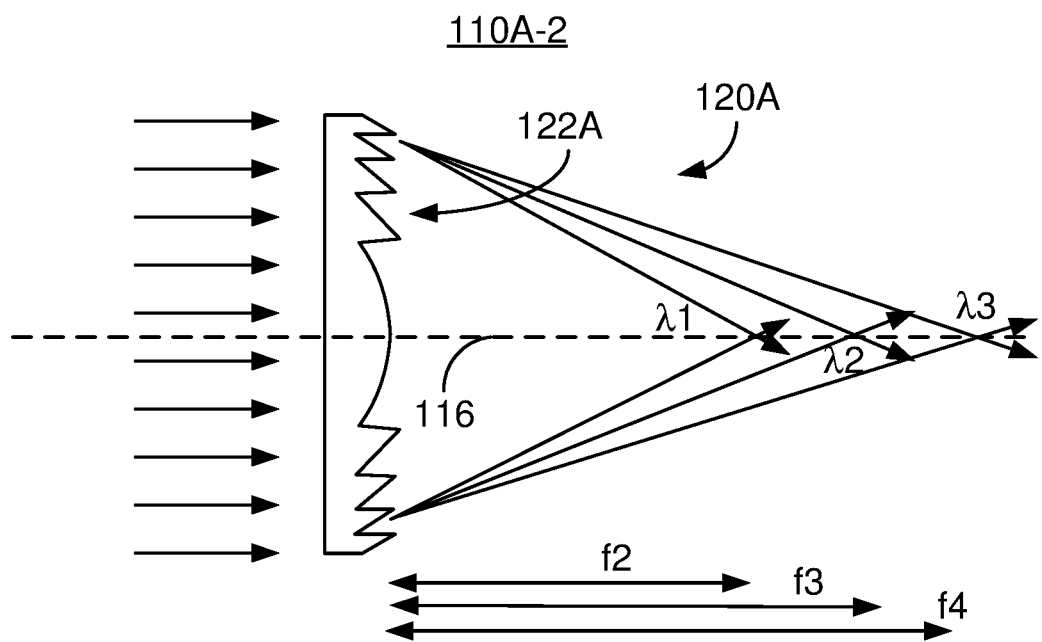

FIGS. 1A-1D depict an exemplary embodiment of an ophthalmic device 100 that may be used as an IOL and ray diagrams for portions of the ophthalmic device. Consequently, the ophthalmic device 100 is also termed an IOL 100. FIG. 1A depicts a plan view of the IOL 100, which includes a hyperchromatic ophthalmic lens 110A and haptics 102 and 104 FIG. 1B depicts a side view of the ophthalmic lens 110A. FIGS. 1C and 1D depict the ray diagrams illustrating the operation of the hyperchromatic lens 110A. For clarity, FIGS. 1A-1D are not to scale, for explanatory purposes only and depict only some features. The hyperchromatic lens 110A may be made of a variety of optical materials including but not limited to one or more of silicone, a hydrogel, an acrylic and AcrySof®. Haptics 102 and 104 are used to hold the IOL 100 in place in a patient's eye (not explicitly shown). In other embodiments, other mechanism(s) might be used to retain the ophthalmic device in position in the eye. Thus, the haptics 102 and/or 104 might be omitted. For clarity, the haptics are not depicted in the remaining drawings. Although the lens hyperchromatic 110A is depicted as having a circular cross section in the plan view of FIG. 1A, in other embodiments, other shapes may be used. Although described in the context of an IOL, the hyperchromatic lens 110A may be a contact lens or other lens. In such a case, the haptics 102 would be omitted and the lens 110A sized and otherwise configured to reside on the surface of the eye.

The hyperchromatic lens 110A may be a single focus lens. Alternatively, the hyperchromatic lens 110A might be a multifocal lens. The hyperchromatic lens 110A has an anterior surface 112 a posterior surface 114 and an optic axis 116. The lens 110A has a diffractive structure 120A and is also characterized by a base curvature 130A for the anterior surface 112 and base curvature 132A for the posterior surface 114. The base curvatures 130A and 132A may be the same or different. The hyperchromatic lens 110A may provide a base power, astigmatism correction and/or other vision correction(s). The hyperchromatic lens 110A may be aspheric and/or toroidal. The hyperchromatic lens 110A may also have other characteristics that are not shown or discussed in detail for simplicity. Although one diffractive structure 120A is shown on the anterior surface 112, the diffractive structure 120A might be located on the posterior surface 114. In still other embodiments, diffractive structures may be located on the anterior surface 112 and the posterior surface 114 such that the combination of both diffractive structures is equivalent to the diffractive structure 120A. Such diffractive structures may be the same or different. Although shown as a physical diffractive structure, in other embodiments, the diffractive structure 120A may be formed by a change in the index of refraction of the lens 110A.

The base curvatures 130A and 132A allow the lens 110A to refract light. Thus, the base curvatures 130A and 132A may be viewed as providing baseline focal length(s) and a base power for the lens 110A. The base power may be defined at a particular wavelength because most lenses have at least some minimal chromatic aberration. The focal length may be defined for a particular wavelength of green or yellow light, which are in the middle of the visible spectrum. For example, the focal length and, therefore, power, due to the base curvatures 130A and 132A of the lens 110A may be defined for 500 nm wavelength (green) light.

The diffractive structure 120A is formed by steps, or echelettes 122A, which diffract light. The echelettes 122A have step heights that correspond to phase differences. The step height of an echelette 122A is the physical step height (h) multiplied by the difference in index of refraction between the lens 110A and the surrounding media ($\Delta n$). In other words, the step height=h·$\Delta n$. The phase difference, $\phi$, for an echelette 124A is proportional to the step height divided by the wavelength, $\lambda$. More specifically, $\phi=(2 \cdot \pi \cdot h \cdot \Delta n)/\lambda$.

The diffractive structure 120A adds a power to the hyperchromatic lens 110A and introduces a significant chromatic aberration. The power added by the diffractive structure 120A may be evaluated at the same wavelength of light as for the base curvatures 130A and 132A. For example, as the power may be defined by the focal length at a particular wavelength of green or yellow light. For light of a different wavelength, such as red light, the difference in the focal length due to chromatic aberration may be large. The difference in powers for two different wavelengths is the chromatic aberration of the diffractive structure 120A. The chromatic aberration introduced by the diffractive structure 120A should be at least two diopters. In some embodiments, the chromatic aberration introduced is at least three diopters. The diffractive structure 120A may be configured such that not more than five diopters of chromatic aberration are introduced.

The total power of the hyperchromatic lens 110A is due to powers of the base curvatures 130A and 132A and the power of the diffractive structure 120A. Similarly, the total chromatic aberration of the hyperchromatic lens 110A is a combination of the chromatic aberrations due to refraction by the base curvatures 130A and 130B and the diffraction by the diffractive structure 120A. The total chromatic aberration of the hyperchromatic lens 110A is at least two diopters. In some cases, the total chromatic aberration of the hyperchromatic lens 110A is at least three diopters. In some embodiments, the maximum chromatic aberration of the hyperchromatic lens 110A is not more than five diopters.

The functioning of the hyperchromatic lens 110A may be further understood with respect to FIGS. 1C and 1D. FIGS. 1C and 1D are ray diagrams illustrating the functioning of the hyperchromatic lens 110A. The lens 110A may be viewed as including a refractive portion 110A-1 depicted in FIG. 1C and a diffractive portion 110A-2 depicted in FIG. 1D. The refractive portion 110A-1 corresponds to the base curvatures 130A and 132A. The diffractive portion 110A-2 corresponds to the diffractive structure 120A. FIGS. 1C and 1D are, however, for explanatory purposes only.

Referring to FIG. 1C, refraction due to the shape of lens 110A-1 and, therefore, due to the base curvatures 130A and 132A results in a focal length f1 and a corresponding power, p1. For example, assume that this power is 5 diopters. The chromatic aberration due to the refractive portion 110A-1 is generally nonzero, but assumed to be negligible for explanatory purposes. The chromatic aberration due to the refractive portion 110A-1 is generally desired to be significantly smaller than that introduce by the diffractive portion 110A-2. Alternatively, the focal length f1 may be considered to be for a particular wavelength, such as $\lambda 2$, discussed below. Any chromatic aberration introduced by the refractive portion 110A-1 may be combined with the chromatic aberration due to the diffractive portion 110A-2.

The diffractive structure 120A adds a power and a large chromatic aberration. The focal length may be given by $f=r1^2/\lambda$, where r1 is the radius of the first zone for the diffractive structure 120A and $\lambda$ is the wavelength. Light of three different wavelengths λ1, λ2 and λ3 is focused at focal lengths f2, f3 and f4, respectively, by the diffractive portion 110A-2. The diffractive portion 110A-2 has powers p2, p3 and p4 for wavelengths λ1, λ2 and λ3, respectively. The powers p2, p3 and p4 correspond to focal lengths f2, f3 and f4, respectively. Suppose that λ2 is five hundred nanometers (green light), λ1 is six hundred nanometers (red light) and λ3 is four hundred nanometers (violet light). The ray diagram of FIG. 1D thus represents most of the visible spectrum.

The difference in power between two specified wavelengths is the chromatic aberration for the diffractive portion 110A-1. The difference in power for the wavelengths λ2 and λ3 represent the difference in power between roughly the middle of the visible spectrum and one end of the visible spectrum. Thus, this difference in power is considered the chromatic aberration for the diffractive portion 110A-2 in this example. The middle of the visible spectrum may also be considered to be the baseline for this power difference in order to ensure that distance vision is corrected as desired. Other wavelengths and power differences, such as p3−p2, might be used in other cases. The chromatic aberration for the diffractive portion 110A-1 is at least two diopters (p3−p4≥2 diopter). In some cases, chromatic aberration for the diffractive portion 110A-1 is at least three diopters (p3−p4≥3 diopter). In some embodiments, the maximum chromatic aberration of the diffractive portion 110A-2 is not more than five diopters (p3−p4≥≤3 diopter). For explanatory purposes, assume p4 is twelve diopters, p3 is fifteen diopters and p2 is eighteen diopters. Thus, the chromatic aberration for the diffractive portion 110A-2 is ±three diopters in this example.

The total corrective power provided by the hyperchromatic lens 110A may be the sum of the power for the refractive portion 110A-1/base curvatures 130A and 1306 and the power for the diffractive portion 110A-2/diffractive structure 120A. Thus, the power for the hyperchromatic lens 110A may be p1+p3=5 diopter plus 15 diopters=20 diopters. Thus, the hyperchromatic lens 110A may provide twenty diopters of power for visual correction. As discussed above, the twenty diopters may be considered to be the baseline power provided by the hyperchromatic lens 110A in order to ensure that longer distance vision is corrected as desired. In addition, there is a large chromatic aberration of three diopter between λ2 and λ3. This chromatic aberration is due to the diffractive portion 110A-2. This large chromatic aberration is what makes the lens 110A a "hyperchromatic" lens.

The hyperchromatic lens 110A may be used to treat presbyopia. More specifically, the chromatic aberration of the hyperchromatic lens 110A may be used in correcting near vision. In the retina, cone cells are responsible for sensing color. S (short wavelength), M (medium wavelength) and L (long wavelength) cone cells may be considered to detect blue, green and red light, respectively. At least some processing of color detected by S, M and L cone cells is performed locally. In addition to being sensed separately, this local processing may be implemented separately for different wavelengths. The processed data may then be sent to the brain. It is believed that the brain tends to recognize the sharpest image provided by the cone cells. For example, suppose the (red) image provided by the L cone cells is sufficiently sharper than the (green) image and (blue) image provided by the M and S cone cells. The brain may then tend to recognize the red image as the valid image and ignore the green and blue images.

The chromatic aberration in the hyperchromatic lens 110A may provide an additional two, three or more diopter of correction using longer wavelength light. Because of the large chromatic aberration, the longer wavelength light may be focused on the retina for near vision even though the short and medium wavelengths are not. The L cone cells may sense this in-focus image, while the S and M cells sense the out-of-focus blue and green images. Although the image sensed by the L cone cells may be shifted toward the red end of the visual spectrum, it may still be selected by the brain as the appropriate image because this image is in focus while the images from other wavelengths of light are not. The patient "sees" the in-focus red-shifted image. Thus, the hyperchromatic lens 110A may be able to assist a patient in correcting near vision for patients having presbyopia.

The ophthalmic device 100 and hyperchromatic lens 110A may provide improved visual acuity and may be used to treat conditions such as presbyopia. As discussed above, the large chromatic aberration introduced by the diffractive structure 120A may correct for the absence of accommodation by the patient's lens. Stated differently, the depth of focus for the hyperchromatic lens 110A may be extended by the large chromatic aberration. This can be achieved without the high x/y position accuracy required by many multifocal IOLs. For example, ±1 mm may be sufficient. Further, the energy distribution for the hyperchromatic lens 110A is independent of pupil size. Consequently, contraction and expansion of the pupil to account for changing illumination conditions may not adversely affect performance of the hyperchromatic lens 110A. Thus, placement and performance of the hyperchromatic lens 110A may be improved.

Figure 2:
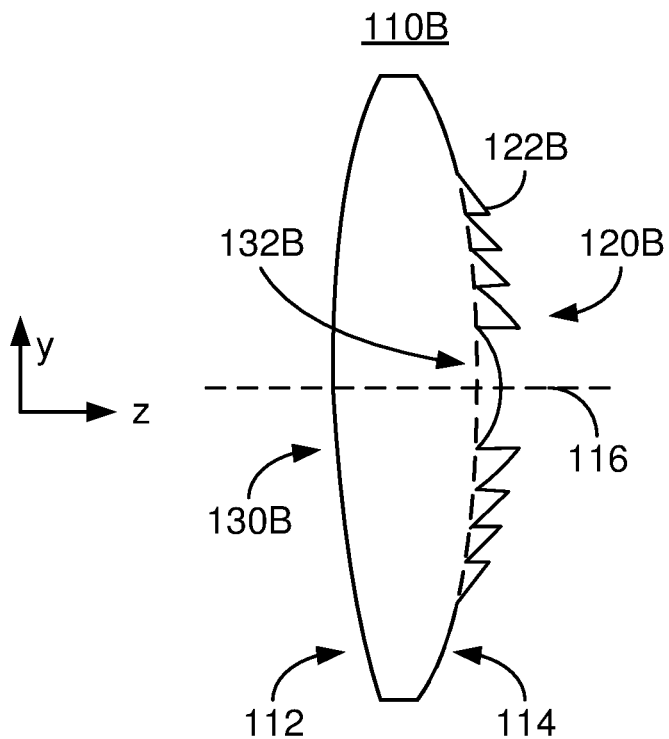
FIG. 2 depicts another exemplary embodiment of a hyperchromatic lens for use in an ophthalmic device.

FIG. 2 depicts another exemplary embodiment of a hyperchromatic lens 110B that may be used in an ophthalmic device such as the IOL 100. For clarity, FIG. 2 is not to scale and not all components may be shown. The hyperchromatic lens 110B is analogous to the hyperchromatic lens 110A. Consequently, analogous components have similar labels. Thus, the hyperchromatic lens 110B includes an anterior surface 112, a posterior surface 114, an optic axis 116, a diffractive structure 120B and base curvatures 130B and 132B that are analogous to the anterior surface 112, the posterior surface 114, the optic axis 116, the diffractive structure 120A and base curvatures 130A and 132A. The hyperchromatic lens 110B functions in an analogous manner to the hyperchromatic lens 110A.

The hyperchromatic lens 110B may be a single focus lens. Alternatively, the hyperchromatic lens 110A might be a multifocal lens. The hyperchromatic lens 110B may provide a base power, astigmatism correction and/or other vision correction(s). The hyperchromatic lens 110B may be aspheric and/or toroidal, have the same or different base curvatures 130B and 132B on the surfaces 112 and 114, respectively and/or other characteristics that are not shown or discussed in detail for simplicity. Although one diffractive structure 120B is shown, multiple the diffractive structures might be located on the surfaces 112 and 114. Diffractive structures may be located on the anterior surface 112 and the posterior surface 114 such that the combination of both diffractive structures is equivalent to the diffractive structure 120B. Such diffractive structures may be the same or different. Although shown as a physical diffractive structure, in other embodiments, the diffractive structure 120B may be formed by a change in the index of refraction of the lens 110B.

The base curvatures 130B and 132B allow the lens 110B to refract light. Thus, the base curvatures 130B and 132B may be viewed as providing baseline focal length(s) and a base power for the lens 110B. The base power may be defined at a particular wavelength because most lenses have at least some minimal chromatic aberration. If the lens 110B is a single focal length lens, then the focal length may be defined for a particular wavelength of green or yellow light, which are in the middle of the visible spectrum.

The diffractive structure 120B includes echelettes 122B. The diffractive structure 120B adds a power and a large chromatic aberration to the hyperchromatic lens 110B. The chromatic aberration introduced by the diffractive structure 120B is at least two diopters. In some embodiments, the chromatic aberration introduced is at least three diopters. The diffractive structure 120B may be configured such that not more than five diopters of chromatic aberration are introduced.

The total power of the hyperchromatic lens 110B is due to powers of the base curvatures 130B and 132B and the power of the diffractive structure 120A. Similarly, the total chromatic aberration of the hyperchromatic lens is a combination of the chromatic aberrations due to refraction by the base curvatures 130B and 130B and the diffraction by the diffractive structure 120B. The total chromatic aberration of the hyperchromatic lens 110B is at least two diopters. In some cases, the total chromatic aberration of the hyperchromatic lens 110B is at least three diopters. In some embodiments, the maximum chromatic aberration of the hyperchromatic lens 110B is not more than five diopters.

The hyperchromatic lens 110B may have improved performance. The hyperchromatic lens 110B may be used to treat conditions such as presbyopia via the large chromatic aberration introduced by the diffractive structure 120B. This correction can be achieved without the high x/y position accuracy required by many multifocal IOLs. The energy distribution for the hyperchromatic lens 110B is also independent of pupil size. Thus, placement and performance of the hyperchromatic lens 110B and visual acuity of the patient may be improved.

Figure 3:
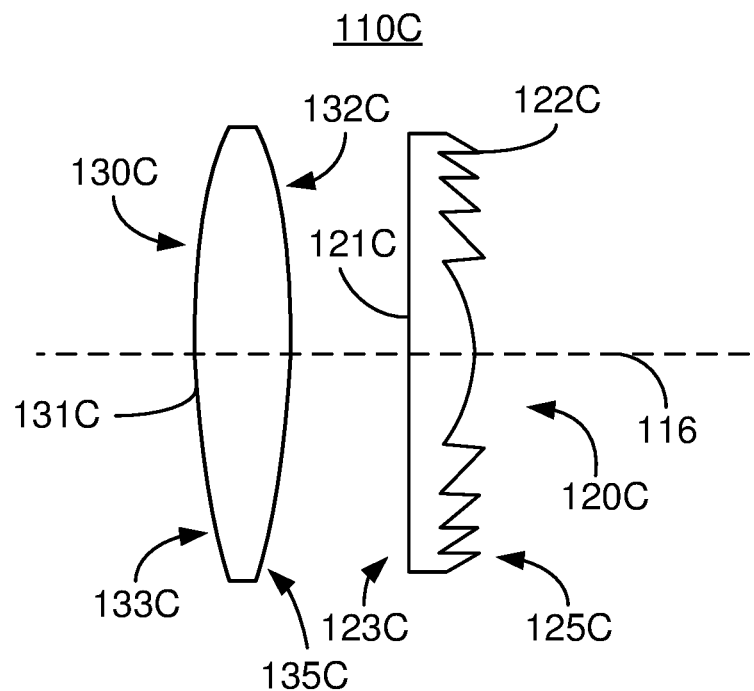
FIG. 3 depicts another exemplary embodiment of a hyperchromatic lens combination for use in an ophthalmic device.

FIG. 3 depicts another exemplary embodiment of a hyperchromatic lens combination 110C that may be used in an ophthalmic device such as the IOL 100. For clarity, FIG. 3 is not to scale and not all components may be shown. Thus, the hyperchromatic lens combination 110C includes a first lens 131C and a second lens 121C. Although a combination of lenses 131C and 121C are used, the combination 110C is also termed a lens 110C. The hyperchromatic lens 110C is analogous to the hyperchromatic lens(es) 110A and 110B. Consequently, analogous components have similar labels and functions. The first lens 131C includes anterior surface 133C, and posterior surface 135C having base curvatures 130C and 132C, respectively. The second lens 121C includes anterior surface 123C, posterior surface 125C and diffractive structure 120C having echelettes 122C. The lenses 131C and 121C share an optic axis 116. The optic axis 116, base curvatures 130C and 132C and diffractive structure 120C are analogous to the optic axis 116, base curvatures 130A, 130B, 132A and 132B and diffractive structures 120A and 120B, respectively.

The lenses 131C and 121C together function in an analogous manner to the hyperchromatic lenses 110A and 110B. The base curvatures 130C and 132C are present on one lens 131C, while the diffractive structure 120C is present on the other lens 121C. The base curvatures 130C and 132C refract light. Thus, the base curvatures 130C and 132C may be viewed as providing baseline focal length(s) and a base power for the lens 110C. The base power may be defined at a particular wavelength because most lenses have at least some minimal chromatic aberration. The focal length may be defined for a particular wavelength of green or yellow light, which are in the middle of the visible spectrum.

The diffractive structure 120C includes echelettes 122C and adds both a power and a large chromatic aberration to the hyperchromatic lens 110C. The chromatic aberration introduced by the diffractive structure 120C is at least two diopters. In some embodiments, the chromatic aberration introduced is at least three diopters. The diffractive structure 120C may be configured such that not more than five diopters of chromatic aberration are introduced.

The total power of the hyperchromatic lens 110C is due to powers of the base curvatures 130C and 132C of one lens 131C and the power of the diffractive structure 120C of the other lens 121C. Similarly, the total chromatic aberration of the hyperchromatic lens is a combination of the chromatic aberrations due to refraction by the base curvatures 130C and 130C of one lens 131C and the diffraction by the diffractive structure 120C of the other lens 121C. The total chromatic aberration of the hyperchromatic lens 110C is at least two diopters. In some cases, the total chromatic aberration of the hyperchromatic lens 110C is at least three diopters. In some embodiments, the maximum chromatic aberration of the hyperchromatic lens 110C is not more than five diopters.

The hyperchromatic lens 110C may have improved performance. The hyperchromatic lens 110C may be used to treat conditions such as presbyopia via the large chromatic aberration introduced by the diffractive structure 120C. This correction can be achieved without the high x/y position accuracy required by many multifocal IOLs. The energy distribution for the hyperchromatic lens 110C is also independent of pupil size. Thus, placement and performance of the hyperchromatic lens 110C and visual acuity of the patient may be improved. However, because two lenses 131C and 121C are used, one lens may be an IOL while the other may be a contact lens.

Figure 4:
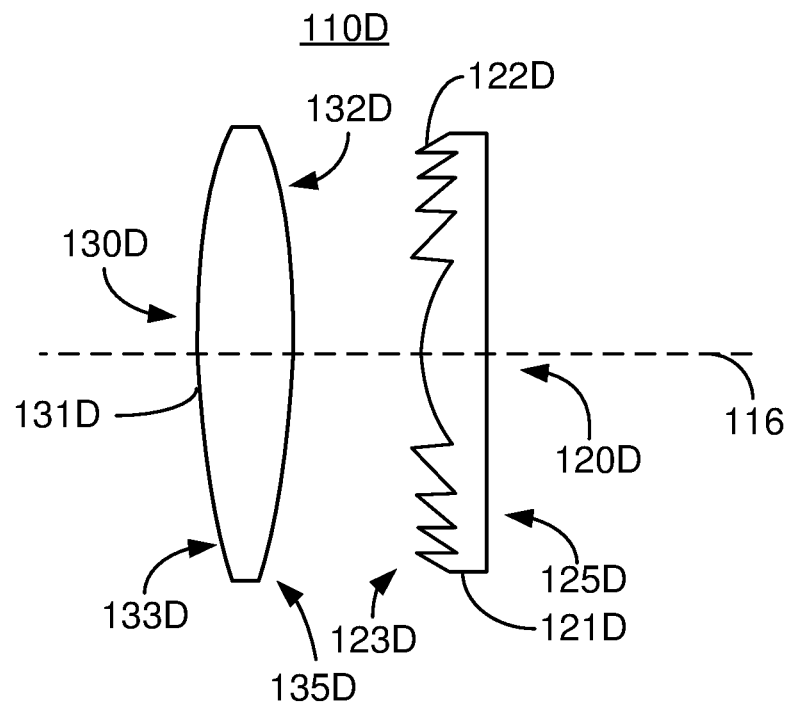
FIG. 4 depicts another exemplary embodiment of a hyperchromatic lens combination for use in an ophthalmic device.

FIG. 4 depicts another exemplary embodiment of a hyperchromatic lens combination 110D that may be used in an ophthalmic device such as the IOL 100. For clarity, FIG. 4 is not to scale and not all components may be shown. Thus, the hyperchromatic lens combination 110D includes a first lens 131D and a second lens 121D. Although a combination of lenses 131D and 121D are used, the combination 110D is also termed a lens 110D. The hyperchromatic lens 110D is analogous to the hyperchromatic lens(es) 110A, 110B and 110C. Consequently, analogous components have similar labels and functions. The first lens 131D includes anterior surface 133D, and posterior surface 135D having base curvatures 130D and 132D, respectively. The second lens 121D includes anterior surface 123D, posterior surface 125D and diffractive structure 120D having echelettes 122D. The lenses 131D and 121D share an optic axis 116. The optic axis 116, base curvatures 130D and 132D and diffractive structure 120D are analogous to the optic axis 116, base curvatures 130A, 130B, 130C, 132A, 132B and 132C and diffractive structures 120A, 120B and 120C, respectively.

The lenses 131D and 121D together function in an analogous manner to the hyperchromatic lenses 110A, 110B and 110C. The lenses 131D and 121D are most analogous to the lenses 131C and 121C, respectively. However, the diffractive structure 120D is on the anterior side 123D of the lens 121D, instead of the posterior side 125D.

The hyperchromatic lens 110D may share the benefits of the hyperchromatic lenses 110A, 110B and 110C. The hyperchromatic lens 110D has a large chromatic aberration that may be used to treat conditions such as presbyopia. This correction can be achieved without requiring high x/y position accuracy and may be independent of pupil size. Thus, placement and performance of the hyperchromatic lens 110D and visual acuity of the patient may be improved. However, because two lenses 131D and 121D are used, one lens may be an IOL while the other may be a contact lens.

Figure 5:
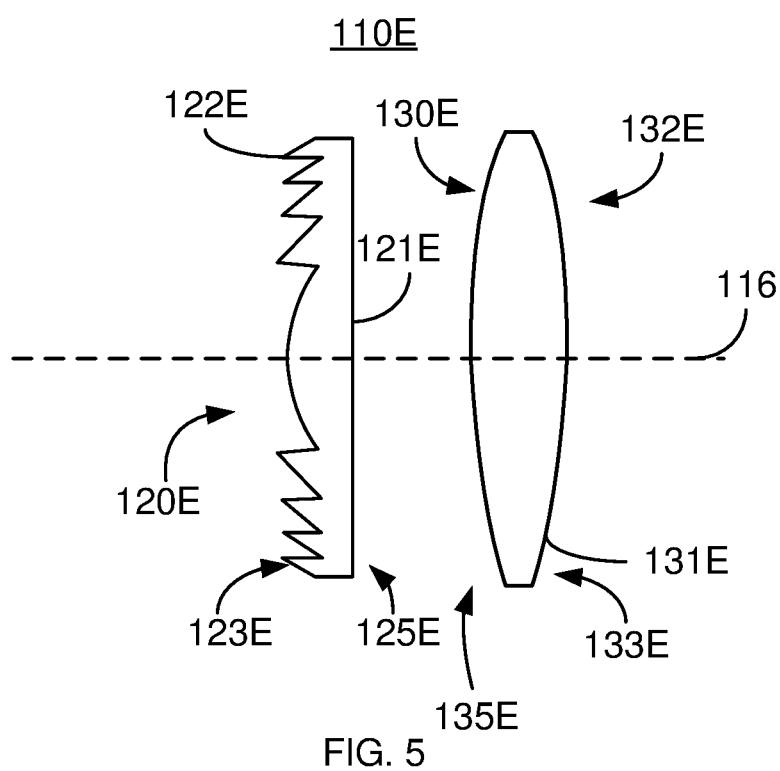
FIG. 5 depicts another exemplary embodiment of a hyperchromatic lens combination for use in an ophthalmic device.

FIG. 5 depicts another exemplary embodiment of a hyperchromatic lens combination 110E that may be used in an ophthalmic device such as the IOL 100. For clarity, FIG. 5 is not to scale and not all components may be shown. Thus, the hyperchromatic lens combination 110E includes a first lens 121E and a second lens 131E. Although a combination of lenses 121E and 131E are used, the combination 110E is also termed a lens 110E. The hyperchromatic lens 110E is analogous to the hyperchromatic lens(es) 110A, 110B, 110C and 110D. Consequently, analogous components have similar labels and functions. The first lens 121E includes anterior surface 123E, posterior surface 125E and diffractive structure 120E having echelettes 122E. The second lens 131E includes anterior surface 133E, and posterior surface 135E having base curvatures 130E and 132E, respectively. The lenses 131E and 121E share an optic axis 116. The optic axis 116, base curvatures 130E and 132E and diffractive structure 120E are analogous to the optic axis 116, base curvatures 130A, 130B, 130C, 130D, 132A, 132B, 132C and 132D and diffractive structures 120A, 120B, 120C and 120D, respectively.

The lenses 131E and 121E together function in an analogous manner to the hyperchromatic lenses 110A, 110B, 110C and 110D. The lenses 131E and 121E are most analogous to the lenses 131C and 121C, respectively. However, the diffractive structure 120E is on the first lens 121E, while the base curvatures 130A and 132E are on the second lens. Operation, however, is substantially the same.

The hyperchromatic lens 110E may share the benefits of the hyperchromatic lenses 110A, 110B, 110C and 110D. The hyperchromatic lens 110E has a large chromatic aberration that may be used to treat conditions such as presbyopia. This correction can be achieved without requiring high x/y position accuracy and may be independent of pupil size. Thus, placement and performance of the hyperchromatic lens 110E and visual acuity of the patient may be improved. However, because two lenses 131E and 121E are used, one lens may be an IOL while the other may be a contact lens.

Various features of the hyperchromatic lenses 110A, 110B, 110C, 110D and 110E have been described herein. One of ordinary skill in the art will recognize that one or more of these features may be combined in manners not explicitly disclosed herein and that are not inconsistent with the apparatus described.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An ophthalmic device comprising:
   at least one ophthalmic lens having at least one base focal length and a base power; and
   at least one diffractive structure for the at least one ophthalmic lens, the at least one diffractive structure configured to induce a chromatic aberration such that the ophthalmic device transmits a first wavelength of visible light at a first power and a second wavelength of visible light at a second power;
   wherein a difference between the first power and the second power is at least two diopters, thereby providing an extended depth of focus across a spectrum of visible light between the first wavelength and the second wavelength.

2. The ophthalmic device of claim 1, wherein the at least one focal length includes a plurality of focal lengths such that the at least one ophthalmic lens is a multifocal lens.

3. The ophthalmic device of claim 1, wherein the difference is at least three diopters and not more than five diopters.

4. The ophthalmic device of claim 1, wherein the first wavelength of visible light is at least four hundred ninety nanometers and not more than five hundred and ten nanometers and the second wavelength of visible light is at least five hundred ninety nanometers and not more than six hundred and ten nanometers.

5. The ophthalmic device of claim 1, wherein the first wavelength of visible light is not more than two hundred nanometers from the second wavelength of visible light.

6. The ophthalmic device of claim 1, wherein the at least one base focal length has a base chromatic aberration corresponding for a base chromatic aberration power and wherein a combination of the base chromatic aberration power and the difference between the first power and the second power is at least two diopters.

7. The ophthalmic device of claim 1, wherein the base power corresponds to a base curvature of the at least one ophthalmic lens.

8. The ophthalmic device of claim 1, wherein the at least one diffractive structure is incorporated into an anterior surface of the at least one ophthalmic lens.

9. The ophthalmic device of claim 1 wherein the at least one diffractive structure is incorporated into a posterior surface of the at least one ophthalmic lens.

10. The ophthalmic device of claim 1, wherein the at least one ophthalmic lens is selected from an intraocular lens and a contact lens.

11. The ophthalmic device of claim 1, wherein the at least one ophthalmic lens includes a first lens and a second lens, the first lens having the base power, the second lens having the at least one diffractive structure.

12. The ophthalmic device of claim 1, wherein the at least one ophthalmic lens is a single lens having the base power and the at least one diffractive structure.

13. An ophthalmic device comprising:
   an ophthalmic lens having at least one base focal length and at least one base power, the ophthalmic lens including an anterior surface and a posterior surface, the at least one base power corresponding to at least one base curvature of at least one of the anterior surface and the posterior surface, the ophthalmic lens further comprising a diffractive structure configured to induce a chromatic aberration such that the ophthalmic lens transmits a first wavelength of visible light at a first power and a second wavelength of visible light at a second power, wherein a difference between the first power and the second power is at least three diopters and not more than five diopters, thereby providing an extended depth of focus across a spectrum of visible light between the first wavelength and the second wavelength; and
   a plurality of haptics coupled with the ophthalmic lens.

* * * * *